(12) United States Patent
Padegimas et al.

(10) Patent No.: US 6,703,541 B1
(45) Date of Patent: Mar. 9, 2004

(54) NEMATODE-UPREGULATED PEROXIDASE GENE PROMOTER FROM NEMATODE-RESISTANT MAIZE LINE MP307

(75) Inventors: Linas S. Padegimas, Starkville, MS (US); Nancy A. Reichert, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 09/716,410

(22) Filed: Nov. 21, 2000

Related U.S. Application Data
(60) Provisional application No. 60/167,229, filed on Nov. 24, 1999.

(51) Int. Cl.$^7$ .................. C12N 15/09; C12N 15/29; C12N 15/82; C12N 15/31; A01H 5/00

(52) U.S. Cl. .................. 800/279; 800/278; 800/287; 800/320.1; 800/288; 435/419; 435/468; 435/320.1; 536/23.6; 536/23.2; 536/23.7; 536/24.1

(58) Field of Search .................. 800/279, 278, 800/287, 320.1, 288; 435/320.1, 419, 468; 536/23.2, 23.6, 23.7, 24.1

(56) References Cited

U.S. PATENT DOCUMENTS

| | | | |
|---|---|---|---|
| 5,051,255 A | 9/1991 | Devidas et al. | |
| 5,750,386 A | 5/1998 | Conkling et al. | |
| 5,965,387 A | 10/1999 | Jepson et al. | |
| 6,008,436 A | 12/1999 | Conkling et al. | |
| 6,072,103 A | 6/2000 | Wu et al. | |
| 6,093,810 A | 7/2000 | Bird et al. | |
| 6,100,451 A | 8/2000 | Chappell et al. | |
| 6,140,555 A | 10/2000 | Reichert et al. | |

FOREIGN PATENT DOCUMENTS

| | | |
|---|---|---|
| EP | 517367 A1 | 9/1992 |
| WO | WO 92/15690 | 9/1992 |

OTHER PUBLICATIONS

Tyagi, Akhilesh, Current Science (2001), vol. 80 (2), pp. 161–169.*
Kirsch et al. Molecular Plant Pathology (2000), 1(4), pp. 243–251.*
Yamamoto et al. The Plant Cell (1991), vol. 3, pp. 371–382.*
Kim et al. Plant Molecula Biology (1994), vol. 24, pp. 105–117.*
Opperman et al. Science (1994), vol. 263, pp. 221–223.*
Lewin, Benjamin. Genes, Oxford New York, 1997, pp. 1232–1237.*
Chawla, H.S. Introduction to Plant Biotechnology, 2nd Ed. 2002.*
Atkinson HJ: Nematodes. In Gurr SJ, McPherson MJ, Bowles DJ (eds), Molecular Plant Pathology: a practical approach, vol. 1, pp. 99–108. IRL Press, New York, NY (1992).
Aung T, Windham GL, Williams WP: Reproduction of *Meloidogyne incognita* on open–pollinated maize varieties. J Nematol (Suppl) 22(4S):651–653 (1990).
Baldridge GD. O'Neill NR, Samac DA: Alfalfa (*Medicago sativa* L.) Resistance to the root–lesion nematode, *Pratylenchus penetrans*: defense–response gene mRNA and isoflavonoid phytoalexin levels in roots. Plant Mo. Biol 38:999–1010 (1998).
Benfey PN, Chua, N–H: The cauliflower mosaic virus 35S promoter: combinatorial regulation of transcript in plants. Science 250:959–966 (1990).
Bevan M: Binary Agrobacterium vectors for plant transformation. Nucleic Acids Res. 12(22):8711–8721 (1984).
Bird AF: The inducement of giant cells by *Meloidogyne javanica*. Nematologica 8:1–10 (1962).
Boerma HR: An overview of soybean resistance and tolerance to nematodes. Proc Southern Soybean Disease Workers 16:2–3 (1989).
Canto–Sáenz M: The nature of resistance to *Meloidogyne incognita*. In Sasser JN, Carter CC (eds), An Advanced Treatise on Meloidogyne, vol. 1, Biology and Control, pp. 225–231. North Carolina State University Graphics, Raleigh, NC (1985).
Chittoor, JM Leach, JE, White, FF: Differential Induction of a Peroxidase Gene Family During Infection of Rice by Xanthomonas Oryzae PV. Oryza, Mol. Plant Microbe Interact. 10(7):861–871 (1997).
Dowd PF, Herms DA, Berhow MA, Lagrimini LM: Mechanisms of insect resistance in transgenic plants (over)expressing a tobacco anionic peroxidase. Plant Peroxidase Newslett 14:93–101 (1999).
Dropkin VH: Resistance. In Introduction to Plant Nematology, pp. 248–265. John Wiley & Sons, Inc, New York, NY (1989).
Endo BY, Veech JA: The histochemical localization of oxidoreductine enzymes of soybeans infected with the root–knot nematode *Meloidogyne incognita acrita*. Phytopathol. 59:418–425 (1969).

(List continued on next page.)

*Primary Examiner*—Elizabeth F. McElwain
*Assistant Examiner*—Medina A. Ibrahim
(74) *Attorney, Agent, or Firm*—Piper Rudnick LLP; Steven B. Kelber

(57) ABSTRACT

The present invention provides a nematode inducible promoter sequence from maize inbred line Mp307, and DNA constructs and transcription cassettes comprising said promoter sequence, a gene encoding a toxin, and a termination sequence. Methods for inducing nematode resistance in plants and transgenic plants resistant to nematode infection are also provided.

22 Claims, 4 Drawing Sheets

OTHER PUBLICATIONS

Fassuliotis G: Genetic basis of plant resistance to nematodes. In Veech JA, Dickson DW (eds), Vistas on Nematology, pp. 364–371. Society of Nematology, Hyattsville, MD (1987).

Graham, MY,Graham, TL: Rapid accumulation of anionic peroxidases and phenolic polymers in soybean cotyledon tissues following treatment with *Phytophthora megasperma* f. sp. *glycinea* wall glucan, Plant Physiol. 97, 1445–1455 (1991).

Hammond–Kosack KE, Jones DG: Resistance gene–dependent plant defense responses. Plant Cell 8:1773–1791 (1996).

Huang J–S: Mechanisms of resistance to root–knot nematodes. In Sasser JN, Cater CC (eds), An Advanced Treatise on Meloidogyne, Biology and Control, 1:165–175. North Carolina State University Graphics, aleigh, NC (1985).

Hussey RS: Disease–inducing secretions of plant–parasitic nematodes. Ann Rev. Phytopathol 27:123–141 (1989).

Hussey, RS: Host–parasite relationships and associated physiological changes. In Sasser JN, Carter CC (eds), An Advanced Treatise on Meloidogyne, vol. 1, Biology and Control, pp. 143–153. North Carolina State University Graphics, Raleigh, NC (1985).

Hussey, RS and Williamson: Physiological and Molecular Aspects of Nematode Parasitism, Plant and Nematode Interactions, Amer. Society of Agronomy, Inc., p. 87–108(1998).

Kim, K.–Y., Huh, G.–H, Lee, H.–S, Kwon, S.–Y.: Molecular characterization of cDNAs for two anionic peroxidases from suspension cultures of sweet potato, Mol Gen Genet 261:941–947 (1999).

Klotz KL, Liu TY, Liu L, Lagrimini LM: Expression of the tobacco anionic peroxidase gene is tissue–specific and developmentally regulated. Plant Mol Biol. 36:509–520 (1998).

Lagrimini, LM, Burkhart, W, Moyer, M, Rothstein, S: Molecular cloning of complementary DNA encoding the lignin–forming peroxidase from tobacco: Molecular analysis and tissue–specific expression, Proc. Natl. Acad. Sci. vol. 84 pp. 7542–7546, (1987).

Lewin, B: *Gene VII*, Oxford University Press, pp. 49–52 (2000).

Price NS, Clarkson DT, Hague NJ: Effect of invasion by cereal–cyst nematode (*Heterodea avenae*) on the growth and development of the seminal roots of oats and barley. Plant Pathol 32:377–83 (1983).

Padegimas, LS and Reichert, NA: Adaptor Ligation–based polymerase chain reaction–mediated walking, Analytical Biochemistry 260:149–153, Article No. AB982719 (1998).

Poehlman, J: Breeding Field Crops, Third Edition, Published by VanNostrand Reinhold, New York, pp. 451–507 (1987).

Sambrook J, Fritsch EF, Maniatis T: A Laboratory Manual, Second Edition. In Molecular Cloning, Cold Spring Harbor Laboratory Press, Cold Spring Harbor, NY (1989).

Sasser JN: Pathogenicity, host ranges and variability in Meloidogyne species. In Lamberti F, Taylor CE (eds), Root–knot nematodes (Meloidogyne species), pp. 257–268. Academic Press, New York, NY (1979).

Sasser JN, Carter CC: Overview of the international Meloidogyne project 1975–1984 In Sasser, JN and CC Carter eds. An Advanced Treatise on Meloidogyne vol. 1 Biology and Control pp. 19–24. NC State Univ Graphics, Raleigh, NC (1985).

Schweizer, Partick, Hunziker, W., Mosinger, E.: cDNA cloning, in vitro transcription and partial sequence analysis of mRNAs from winter wheat (*Triticum aestivum* L.) with induced resistance to *Erysiphe graminis* f. sp. *tritici*, Plant Molecular Biology 12:643–654 (1989).

Sijmons, P.C., Atkinson, H.J., Wyss, U.: Parasitic strategies of root nematodes and associated host cell responses, Annu. Rev. Phytopathol. 32:235–259 (1994).

Stintzi, A., Heintz, T., Prasad, V., Wiedemann–Merdinoglu, S., Kauffmann, S., Geoffroy, P., Legrand, M., Fritig, B.: Plant pathogenesis–related proteins and their role in defense against pathogens, Biochimie 75:687–706 (1993).

Tomes DT, Weissinger AK, Ross M, Higgins R, Drummond BJ, Schaaf S, Malone–Schoneberg J, Staebell M, Flynn P, Anderson J and Howard J: Transgenic tobacco plants and their progeny derived by microprojectile bombardment of tobacco leaves. Plant Mol. Biol. 14:261–268 (1990).

Trudgill DL: Effects of *Globodera rostochiensis* and fertilizers on the mineral nutrient content and yield of potato plants. Nematologica 26:243–54 (1980).

Trudgill DL: Resistance to and tolerance of plant parasitic nematodes in plants. Annu. Rev. Phytopathol. 29:167–192 (1991).

Trudgill DL, Evans K, Parrott DM: Effects of potato–cyst nematodes on potato plants: Effects in trials with irrigation and fumigation on the growth and nitrogen and potassium contents of a resistant and susceptible variety. Nematologica 21: 169–82 (1975).

Veech JA, Endo BY: The histochemical localization of several enzymes of soybean infected with the root–knot nematode *Meloidogyne incognita acrita*. J Nematol 1:265–276 (1969).

Von Mende, N.: Invasion and migration behaviour of sedentary nematodes, C. Fenoll et al. (eds), Cellular and Molecular Aspects of Plant Nematode Interactions, p. 51–64 (1997).

Vos, P, Simons, G, Jesse, T, Wijbrandi, J, Heinen, L, Hogers, R, Frijters, A, Groenendijk, J, Diergaarde, P, Reijans, M, Fierens–Onstenk, J, de Both, M, Peleman, J, Liharska, T, Hontelez, J, Zabeau, M: the tomato Mi–1 gene confers resistance to both root–knot nematodes and potato aphids, Nature Biotechnology, 16:1365–1369 (1998).

Walton JD: Biochemical plant pathology. In Dey PM, Harborne JB (eds) Plant Biochemistry, pp. 487–502. Academic Press, New York, NH (1997).

Welinder KG: Superfamily of plant, fungal, and bacterial peroxidases. Curr Opin Struct Biol. 2:388–393 (1992).

Wiggers RJ, Starr JL, Price HJ: DNA content and variation in chromosome number in plant cells affected by *Meloidogyne incognita* and *M. arenaria*. Amer. Phytopath. Society 80:1391–1395 (1990).

Williams WP, Windham GL: Resistance of corn to southern root–knot nematode. Crop Sci 28(3):495–496 (1988).

Windham GL, Williams WP: Host suitability of commercial corn hybrids to *Meloidogyne arenaria* and *M. incognita*. Annals of Applied Neimatology 1:13–16 (1987).

Zacheo G, Orlando C, Bleve–Zacheo T: Characterization of anionic peroxidase in tomato isolines infected by *Meloidogyne incognita*. Journal of Nematology, 25(2):249–256 (1993).

* cited by examiner 1  2

FIGURE 3

Sequence name - P7X peroxidase (cDNA sequence).

```
CACACACACCATATCACAAGCAAGCGCCAACGATCGAGCAGAAAGAAGATCGTCGAGATCGAGCATAAGCCATGGCGGCC
TCTGTTTCTGCCTCTTGCCTTATTAGCCTGTCGTCGTTGGCGGTGGTGCTGGTGGCGCTGGCGTCGGCGGCGTCGGCGCA
GCTGTCGTCGACGTTCTACGACAGGTCATGCCCCAACGCGCTGTCCACCATCAGGAGCGGCGTGAACTCCGCGGTGAGGC
AGGAGCCTCGCGTGGGGGCGTCGCTGCTCAGGCTCCATTTCCACGACTGCTTTGTCCGGGGCTGCGACGCGTCCCTTCTG
CTGAACGACACGTCAGGGGAGCAGAGCCAGGGCCCGAATCTAACTCTGAACCCAAGGGGCTTCGTTGTCGTGAACAGCAT
CAAGGCGCAGGTGGAGTCCGTGTGCCCGGGGATCGTCTCCTGCGCCGACATCCTCGCCGTGGCCGCCAGGGACGGAGTCG
TATCGCTCGGCGGGCCTTCGTGGACAGTTCTGCTAGGGCGAAGGGACTCTACCGCTTCATTCCCAGGACAGACAAGCGAC
CCCCCACCTCCGACGTCTAGCCTCCGACAGCTTTTGTCTGCGTATAACAAGAAGAATCTCAACCCAACCGACATGGTTGC
ACTCTCAGGAGCTCACACGATCGGACAGGCGCAGTGCTCGAGCTTCAACGACCACATCTACAACGACACCAACATCAACT
CCGCCTTCGCGGCGTCGCTCAGGGCCAACTGCCCCAGGGCAGGCAGCACCGCCCTTGCGCCGCTGGACACCACGACGCCC
AACGCGTTCGACAACGCCTACTACACCAACCTGCTGTCCCAGAAGGGGCTCCTGCACTCGGACCAGGAGCTCTTCAACAA
CGGCAGCACCGACAGCACGGTCAGGAGCTTCGCGTCCCAGCACGTCGGCCTTCAACAGCGCCTTCGCCACGGCCATGGTC
AAGATGGGCAACCTCAGCCCCCAGACCGGAACCCAGGGGCAGATCAGGCGCAGCTGCTGGAAGGTCAACTCGTAAACTAC
TAGCTACGTACTACGCCCAATGCAATGCGTTATGGCAGGCAGATCAGAGCCAATTAGTAATAAGGCCTCAGCTCGCTCTC
TACCTGTACGTGTGTGTGTGACTGGTGTTGGTCGAGTAAGTGTACGTACTACATGGATGGAGCAGAGAGAGAGAGAGATA
TATCGATTTGGCCACCTTATTATTGCATGCATATGTGTACTGTATTAGCACGACACTATTAGACACATTTATTAATGGTA
CCCATGCTATGCTTGTAAACGTACCCAGCCATTGACCTAGATATGACACTATAGGTCTAATCGTATTGCGGCTAACACCA
AAAAAAAAAAAAAAAAAAA
```

Total length 1379 bp.

Locations/Qualifiers

1...1379
    /P7X peroxidase cDNA sequence
    72...1043
    /sequence encoding   P7X peroxidase

FIGURE 4

Sequence name - P7X peroxidase promoter.

```
ACTCACAACGCTAGCTTCTCTCTATAGTCTATAGAGTGCCGGTCATACCAATTATTTTATGGCACCCGTCGTGTGGCCCT
ATCATATATAAATACATATTTGCATATATTCCTTCTTAGCTACCATACACACAAAATTAGGCTCACGATATGGATGGATG
TTCAGCCATGCCGAGCCGAGCTGGCTTGTTAAAATAACGAACTGACTCGACAAAATCAGCTCAACTCAGTTTGATTGCAA
GTTTGAGCTGACTCGTTTAGCTCGTGAGACATAATAAAAAAATTATATATATAGTAATATATTCGATTACTAGATAGTTA
TAGACTAGTTTAAGACTAAAAAGGAGATATATAATACTCACAATTTCATATGTCGCCTCAATCGAACACCAGATCACAAT
TCATCACTTTTAGTTCATCCAACACAAGTACATGCTCCAGATCACAGTTCATCACTTTTTAGTTCATCCAACACAAGTAC
ATGCTTTGTTTTGCTGACAAATGCATGATTGCTTGTTCGAGCCAACAAGCTGGCTCATTAACAAACCGAGCCGAGATGCT
ACGTCAGCTCGTGATAAAATTCAAACGAACTGATCACATATAAGCCACGAGTATTTTGTCAGCCCTAGCTCATGATGTTA
TCCAGACACCTAACGTATATTGTATCACATGTGGGGCTAGTGTGCGTGTGGCTACCTGTGTACATGCACTGCATGACGAA
AATGGTTATTGCCGGCTTTCAGAGTCTAATTAAATAAATTAGCATGGACGTACTAATAATTCATAAGCTTGACGTCCGGT
TTGGATATATGTTATTTTCTGATCCATAGCTAGCTAGTAGTGACATGCATGCATGCATGATGAAGGCATCATAACATTAC
GGGCCCTAGCTAGCTAATAAATATGCATGTAGTGTATAGCATCGCCTTGCACACACACCATATCACAAGCAAGCGCCAAC
CATCGAGCAGAAAGAAGATCGTCGAGATCGAGCATAAGCCATGGCGGCCTCTGTTTCCGCCTCTTGCCTTATTGGCCTGT
CGTCGTTGGCGGTGGTGCTGGTGGCGCTGGCGTCGGCGGCGTCGGCGCAGCTGTCGTCGACGTTCTACGACAGGTCATGC
CCCAACGCGCTGTCCACCATCAGGAGCGGCGTGAACTCCGCGGTGAGGCAGGAGCCTCGCGTGGGGCGTCGCTGCTCAG
GCTCCATTTCCACGACTGCTTTGTCCGGGCAAGTGAAGTCTCCATCATCTTGCATTCTGCTTTCTTTCTAGAAAACAAAC
ACCAGCAAAATTGAGGGCATTCGTTTAAAAAACTCTAACCCTAAATATTTCTGCAGGGCTGCGACGCGTCCCTTCTGCTG
AAC
```

Total length 1366 bp.

Locations/Qualifiers

1...1000
    /P7X peroxidase promoter
    1001...1228, 1337...1366
    /partial P7X peroxidase coding sequence
    1229...1336
    /intron

SEQUENCE LISTING

<160> NUMBER OF SEQ ID NOS: 10

<210> SEQ ID NO 1
<211> LENGTH: 1379
<212> TYPE: DNA
<213> ORGANISM: Artificial Sequence
<220> FEATURE:
<223> OTHER INFORMATION: cDNA of P7X peroxidase
<220> FEATURE:
<221> NAME/KEY: misc_feature
<222> LOCATION: (1)..(1379)
<223> OTHER INFORMATION: P7X peroxidase cDNA sequence
<220> FEATURE:
<221> NAME/KEY: misc_feature
<222> LOCATION: (72)..(1043)
<223> OTHER INFORMATION: sequence encoding P7X peroxidase

<400> SEQUENCE: 1

```
cacacacacc atatcacaag caagcgccaa cgatcgagca gaaagaagat cgtcgagatc      60
gagcataagc catggcggcc tctgtttctg cctcttgcct tattagcctg tcgtcgttgg     120
cggtggtgct ggtggcgctg gcgtcggcgg cgtcggcgca gctgtcgtcg acgttctacg     180
acaggtcatg ccccaacgcg ctgtccacca tcaggagcgg cgtgaactcc gcggtgaggc     240
aggagcctcg cgtgggggcg tcgctgctca ggctccattt ccacgactgc tttgtccggg     300
gctgcgacgc gtcccttctg ctgaacgaca cgtcagggga gcagagccag ggcccgaatc     360
taactctgaa cccaaggggc ttcgttgtcg tgaacagcat caaggcgcag gtggagtccg     420
tgtgcccggg gatcgtctcc tgcgccgaca tcctcgccgt ggccgccagg gacggagtcg     480
tatcgctcgg cgggccttcg tggacagttc tgctagggcg aagggactct accgcttcat     540
tcccaggaca gacaagcgac cccccacctc cgacgtctag cctccgacag cttttgtctg     600
cgtataacaa gaagaatctc aacccaaccg acatggttgc actctcagga gctcacacga     660
tcggacaggc gcagtgctcg agcttcaacg accacatcta caacgacacc aacatcaact     720
ccgccttcgc ggcgtcgctc agggccaact gccccagggc aggcagcacc gcccttgcgc     780
cgctggacac cacgacgccc aacgcgttcg acaacgccta ctacaccaac ctgctgtccc     840
agaaggggct cctgcactcg gaccaggagc tcttcaacaa cggcagcacc gacagcacgg     900
tcaggagctt cgcgtcccag cacgtcggcc ttcaacagcg ccttcgccac ggccatggtc     960
aagatgggca acctcagccc ccagaccgga acccaggggc agatcaggcg cagctgctgg    1020
aaggtcaact cgtaaactac tagctacgta ctacgcccaa tgcaatgcgt tatggcaggc    1080
agatcagagc caattagtaa taaggcctca gctcgctctc tacctgtacg tgtgtgtgtg    1140
actggtgttg gtcgagtaag tgtacgtact acatggatgg agcagagaga gagagagata    1200
tatcgatttg gccaccttat tattgcatgc atatgtgtac tgtattagca cgacactatt    1260
agacacattt attaatggta cccatgctat gcttgtaaac gtacccagcc attgacctag    1320
atatgacact ataggtctaa tcgtattgcg gctaacacca aaaaaaaaaa aaaaaaaaa     1379
```

<210> SEQ ID NO 2
<211> LENGTH: 1363
<212> TYPE: DNA
<213> ORGANISM: Artificial Sequence
<220> FEATURE:
<223> OTHER INFORMATION: DNA of P7X peroxidase
<220> FEATURE:
<221> NAME/KEY: promoter
<222> LOCATION: (1)..(1000)
<223> OTHER INFORMATION: P7X peroxidase promoter

```
<220> FEATURE:
<221> NAME/KEY: misc_feature
<222> LOCATION: (1001)..(1228)
<223> OTHER INFORMATION: partial P7X peroxidase coding sequence
<220> FEATURE:
<221> NAME/KEY: misc_feature
<222> LOCATION: (1337)..(1363)
<223> OTHER INFORMATION: partial P7X peroxidase coding sequence
<220> FEATURE:
<221> NAME/KEY: Intron
<222> LOCATION: (1229)..(1336)

<400> SEQUENCE: 2
actcacaacg ctagcttctc tctatagtct atagagtgcc ggtcatacca attattttat      60
ggcacccgtc gtgtggccct atcatatata aatacatatt tgcatatatt ccttcttagc     120
taccatacac acaaaattag gctcacgata tggatggatg ttcagccatg ccgagccgag     180
ctggcttgtt aaataacga actgactcga caaaatcagc tcaactcagt ttgattgcaa      240
gtttgagctg actcgtttag ctcgtgagac ataataaaaa aattatatat atagtaatat     300
attcgattac tagatagtta tagactagtt taagactaaa aaggagatat ataatactca     360
caatttcata tgtcgcctca atcgaacacc agatcacaat tcatcacttt tagttcatcc     420
aacacaagta catgctccag atcacagttc atcactttt agttcatcca acacaagtac      480
atgctttgtt ttgctgacaa atgcatgatt gcttgttcga gccaacaagc tggctcatta     540
acaaaccgag cccagatgct acgtcagctc gtgataaaat tcaaacgaac tgatcacata     600
taagccacga gtattttgtc agccctagct catgatgtta ccagacacc taacgtatat      660
tgtatcacat gtggggctag tgtgcgtgtg gctacctgtg tacatgcact gcatgacgaa     720
aatggttatt gccggctttc agagtctaat taaataaatt agcatggacg tactaataat     780
tcataagctt gacgtccggt ttggatatat gttattttct gatccatagc tagctagtag     840
tgacatgcat gcatgcatga tgaaggcatc ataacattac gggccctagc tagctaataa     900
atatgcatgt agtgtatagc atcgccttgc acacacacca tatcacaagc aagcgccaac     960
catcgagcag aaagaagatc gtcgagatcg agcataagcc atggcggcct ctgtttccgc    1020
ctcttgcctt attggcctgt cgtcgttggc ggtggtgctg gtggcgctgg cgtcggcggc    1080
gtcggcgcag ctgtcgtcga cgttctacga caggtcatgc cccaacgcgc tgtccaccat    1140
caggagcggc gtgaactccg cggtgaggca ggagcctcgc gtggggcgt cgctgctcag     1200
gctccatttc cacgactgct ttgtccgggc aagtgaagtc tccatcatct tgcattctgc    1260
tttctttcta gaaaacaaac accagcaaaa ttgagggcat tgctttaaaa aactctaacc    1320
ctaaatattt ctgcagggct gcgacgcgtc ccttctgctg aac                       1363

<210> SEQ ID NO 3
<211> LENGTH: 27
<212> TYPE: DNA
<213> ORGANISM: Artificial Sequence
<220> FEATURE:
<223> OTHER INFORMATION: 3'-RACE cDNA w/Jprim

<400> SEQUENCE: 3
gtgccccaac gcgctgtcca ccatcaa                                           27

<210> SEQ ID NO 4
<211> LENGTH: 35
<212> TYPE: DNA
<213> ORGANISM: Artificial Sequence
<220> FEATURE:
<223> OTHER INFORMATION: 5'-RACE cDNA w/P75w1
```

<400> SEQUENCE: 4
gccctagcag aactgtccac gaaggcccgc cgagc                     35

<210> SEQ ID NO 5
<211> LENGTH: 35
<212> TYPE: DNA
<213> ORGANISM: Artificial Sequence
<220> FEATURE:
<223> OTHER INFORMATION: 5'-cDNA w/P75w2

<400> SEQUENCE: 5
agattcgggc cctggctctg ctcccctgac gtgtc                     35

<210> SEQ ID NO 6
<211> LENGTH: 41
<212> TYPE: DNA
<213> ORGANISM: Artificial Sequence
<220> FEATURE:
<223> OTHER INFORMATION: 5'-RACE cDNA

<400> SEQUENCE: 6
gaagaattct cgagcggccg cttttttttt tttttttttt v              41

<210> SEQ ID NO 7
<211> LENGTH: 21
<212> TYPE: DNA
<213> ORGANISM: Artificial Sequence
<220> FEATURE:
<223> OTHER INFORMATION: 5'-RACE cDNA

<400> SEQUENCE: 7
gaagaattct cgagcggccg c                                    21

<210> SEQ ID NO 8
<211> LENGTH: 33
<212> TYPE: DNA
<213> ORGANISM: Artificial Sequence
<220> FEATURE:
<223> OTHER INFORMATION: oligonucleotide LN

<400> SEQUENCE: 8
cagcagaacg acgccccgcc gacaaggaca ggt                       33

<210> SEQ ID NO 9
<211> LENGTH: 21
<212> TYPE: DNA
<213> ORGANISM: Artificial Sequence
<220> FEATURE:
<223> OTHER INFORMATION: oligonucleotide oligo1
<220> FEATURE:
<221> NAME/KEY: misc_feature
<222> LOCATION: 18,19,20,21
<223> OTHER INFORMATION: nucleotides 18 and 19, 19 and 20, 20 and 21 are
      connected by phosphorothioate linkages

<400> SEQUENCE: 9
acctgtcctg cgaaagcaaa a                                    21

<210> SEQ ID NO 10
<211> LENGTH: 25
<212> TYPE: DNA
<213> ORGANISM: Artificial Sequence
<220> FEATURE:

```
-continued

<223> OTHER INFORMATION: adaptor-specific primer APN

<400> SEQUENCE: 10
cagcagaacg acgcccgcc gacaa                                                    25
```

NEMATODE-UPREGULATED PEROXIDASE GENE PROMOTER FROM NEMATODE-RESISTANT MAIZE LINE MP307

CROSS-REFERENCE TO RELATED APPLICATIONS

This application is a regular National application claiming priority from Provisional Application, U.S. application Ser. No. 60/167,229 filed Nov. 24, 1999. The entirety of that provisional application is incorporated herein by reference.

BACKGROUND OF THE INVENTION

1. Field of the Invention

The present invention relates generally to gene sequences that encode peroxidase genes. In particular, the present invention relates to the isolation and characterization of novel gene sequences which encode the peroxidase P7X gene and promoter isolated from maize inbred line Mp307. Additionally, this invention relates to methods of controlling plant-parasitic nematodes by application of recombinant DNA technology.

2. Background of the Technology

Nematodes are slender, worm-like organisms found in the soil almost anywhere in the world. A significant amount of the world's nematodes are plant parasitic, and are among the most devastating of the numerous pests that infest the world's food crops. Generally, feeding nematodes have complex interactions with their host plants that last more than a month.

Each year, a majority of crop losses are caused by root-knot nematodes such as *Meloidogyne incognita*. Members of this genus have extensive host ranges and can parasitize monocots, dicots (eudicots), herbaceous and woody species, over 2000 different plant species in all (Hussey, 1985). Nematodes have been reported to cause crop loss equivalent to more than $6 billion in the United States and more then $100 billion around the world. (U.S. Pat. No. 5,051,255).

With root-knot nematodes, infection of the plant occurs after juveniles (J2) hatch in the soil, invade the root, and migrate intercellularly to areas of differentiation and begin to set up a feeding site in xylem parenchyma cells in the vascular cylinder (Hussey and Williamson, 1998 and von Mende, 1997). This feeding site is established by injecting glandular secretions into the root cells via the nematode's stylet. (Bleve-Zacheo and Melillo, 1997). The nematode quickly becomes sedentary endoparasites, thereby losing its ability to reinfect. (von Mende, 1997). During this parasitism, plant cells become hypertrophic and multinucleate, which is the result of early nuclear division without cytokinesis. These multinucleate cells, called giant (nurse) cells are formed very early after infection. Eight nuclei can be found within 48 hours of nematode infection. (Wiggers, et al., 1990). The giant cells are metabolically active and serve as the nutritive source for the developing nematode. Qualitative and quantitative changes in giant cell gene expression has been hypothesized to accommodate the demands of the nematode (Bleve-Zacheo and Melillo, 1997). Thus, root-knot nematodes cannot continue to develop normally without the induction and maintenance of these giant cells. (Hussey, 1989).

Various methods have been used to control plant parasitic nematodes. These methods include quarantine measures, manipulation of planting and harvesting dates, improved fertilization and irrigation programs that lessen plant stresses, crop rotation and fallowing, use of resistant and tolerant cultivars and rootstocks, organic soil amendments, and biological and chemical control. (Atkinson, 1992) Today, most of the plant-parasitic nematodes are controlled by chemical nematicides. These compounds are generally very toxic and have been suspected of causing environmental damage. For example, nematicides such as aldicarb, ethoprop, and carbofuran have been determined to be highly toxic to mammals, birds, and fish. Because of this, and the growing concern about the possibility of ground water contamination, several nematicides have had their use restricted or rescinded all together.

Thus, there exists a long felt need for safe and effective methods of protecting plants, particularly crop plants, from infection by plant-parasitic nematodes. Biological or "natural" methods rather than methods dependent on the application of chemicals are especially important from the standpoint of economics and environmental concerns.

SUMMARY OF THE INVENTION

It is an object of the invention to provide an effective and safe means to control plant-parasitic nematodes.

It is also an object of the invention to provide a novel gene sequence which encodes the peroxidase P7X gene isolated from maize inbred line Mp307.

It is yet another object of the invention to provide a novel gene sequence which encodes the upregulated peroxidase-promoter for the peroxidase P7X gene isolated from maize inbred line Mp307.

It is a further object of the invention to provide a method of nematode resistance in plants.

It is an object of the present invention to provide nucleic acid constructs and transcription cassettes which provide for regulated transcription in plant tissue in response to nematode infection.

It is a further object of the invention to provide transgenic plants containing the nucleic acid constructs according to the present invention.

DESCRIPTION OF THE FIGURES

FIG. 3 is the cDNA sequence of P7X peroxidase (SEQ ID NO:1).

FIG. 4 is the DNA sequence of P7X peroxidase promoter (SEQ ID NO:2).

BRIEF DESCRIPTION OF THE INVENTION

Figure 1:
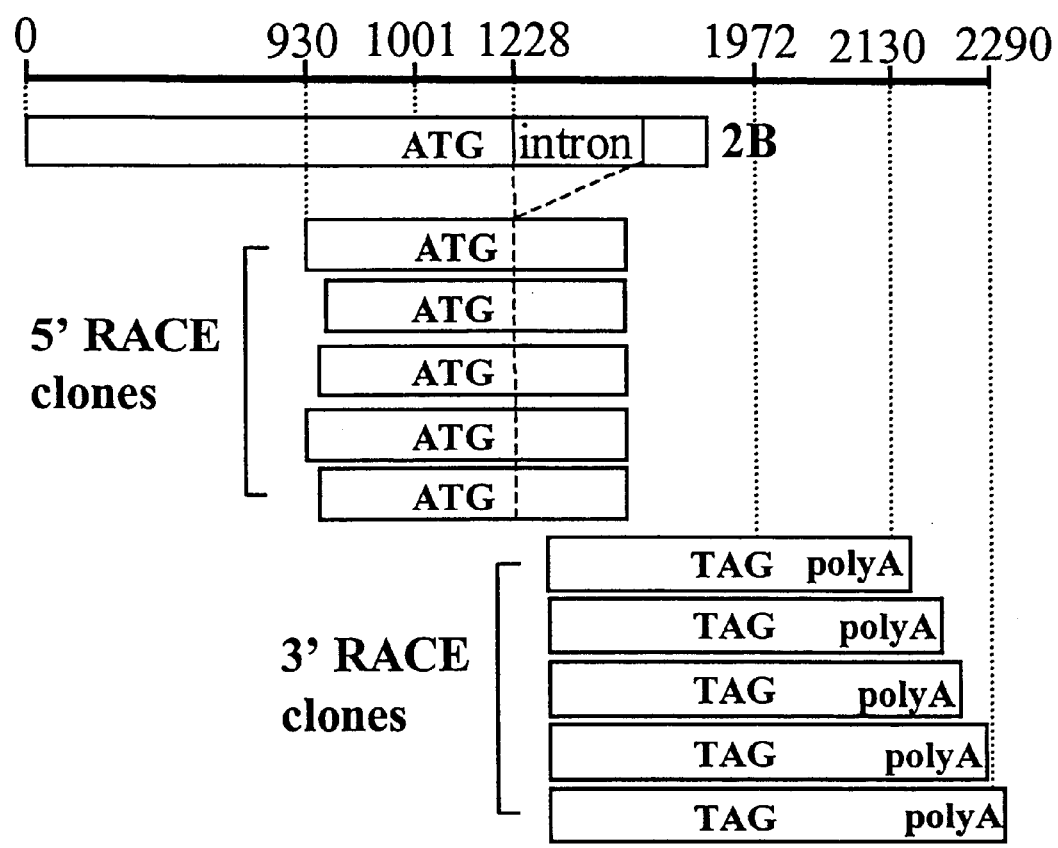
FIG. 1 is a schematic illustration of the assembly of the P7X peroxidase gene using ten clones obtained by RACE and one clone obtained by genomic walking.

The amount of resistance a plant has against nematode infection relates to the plant's effects on nematode reproduction. For example, completely resistant plants do not allow any nematode reproduction, whereas susceptible plants allow nematodes to multiply freely. Recently, studies on host suitability of *M. incognita* have been conducted in corn. Of the 64 commercial *Zea mays* hybrids tested, all were found to be excellent hosts. (Windham, et al., 1987). Only a few of the open pollinated and inbred lines displayed resistances of varying degrees to *M. incognita*. One of the lines that displayed resistance was maize inbred line Mp307 (Aung, et al., 1990 and Williams, et al., 1988), although the mechanism of this resistance is unknown.

Diverse mechanisms have been attributed to plants that exhibit nematode resistance. The genetics of resistance has been traced to single dominant genes and also to recessive or polygenic traits in a variety of plant species. (Fassuliotis, 1987 and Trudgill, 1991). One example of genetic resistance is the tomato. Tomatoes contain a single dominant resistance gene, Mi, which has been recently isolated. (Vos et al., 1998). In addition to genetic resistance, various other mechanisms of resistance have been observed. Examples include hypersensitive responses, like in glyceollin I production (Huang, 1985), and secretion of repellents (cucurbitacins), toxins (α-terthienyl), or other compounds which affect hatching (Dropkin, 1989). Additionally, the ability of nematodes to penetrate roots (Canto-Saenz, 1985) and overall plant nutrition have been demonstrated as determinants of nematode resistance. (Huang, 1985). Because functional giant cells are essential for development of root-knot nematodes, host "unsuitability" may be related to the inability to form these giant cells. (Id.). Other defense response chemicals, including peroxidases, have also been implicated in nematode resistance. (Baldridge, et al., 1998).

Peroxidase is a class of proteins whose primary function is to reduce hydrogen peroxide or molecular oxygen in the presence of an electron donor. (Kim, et al., 1999). Plant peroxidases are known to play a major role in lignin formation and wound healing, and are believed to be involved in auxin catabolism and defense to pathogen attack. (Lagrimini et al., 1987 and Klotz, et al., 1998). Most plants posses numerous peroxidase isoenzymes (isozymes) whose pattern of expression is tissue specific, developmentally regulated, and influenced by environmental factors. (Lagrimini, et al., 1987). These isozymes are usually classified in three groups, anionic (pI 3.5–4.0), moderately anionic (pI 4.5–6.5), and cationic (pI 8.1–11) based on their physical properties, and are believed to perform different functions during plant growth and development (Kim et al., 1999).

Although numerous peroxidase functions remain unknown, there is growing evidence that peroxidases are involved in plant defenses against pathogens and pests. It is believed that peroxidase action can create chemical and physical barriers against invading pathogens via cell wall lignification and protein cross-linking, generation of cytotoxic compounds, and/or oxidizing compounds that are important for pathogen metabolism. (Klotz, et al., 1998). Additionally, peroxidases appear to be intricately related to hypersensitive reactions (HR) in resistant plants. (Hammond-Kosack and Jones, 1996 and Walton, 1997). However, their true physiological roles remain unclear. (Kim, et al., 1999).

A hypersensitive reaction is observed in a resistant plant in response to attempted infection by specific pathogens. The plant's resistance response can include localized plant cell death (HR) plus initiation of a signal transduction cascade which includes the expression of additional host defense genes such as phytoalexins and pathogenesis-related proteins. (Walton, 1997). HR-induced localized cell death is generally restricted to those plant cells immediately adjacent to the infection site, which can restrict and/or limit infection by obligate parasites. Early stages of a hypersensitive reaction are also associated with the generation of activated oxygen species. Activated oxygen species can generate various responses in the plant cells including host cell death, strengthening of cell walls via lignification and protein cross-linking, generation of secondary signals and injury to the invading pathogen. (Id.).

Evidence for peroxidases' roles in pathogen/pest resistance has been noted in various plant species. Increased peroxidase activity has been observed in a number of resistant interactions involving plant-pathogenic fungal and bacterial interactions. (Schweizer, et al., 1989; Graham, et al., 1991; and Chittoor, et al., 1997) and have been observed after elicitation with pathogenic organisms. An increased level of anionic peroxidase activity was observed in resistant tomatoes after nematode inoculation. (Zacheo, et al., 1993). Transgenic plants of *Nicotiana tabacum* (tobacco), *N. sylvestris* (ornamental tobacco), *Lycopersicon esculentum* (tomato), *Liquidambar styraciflua* (sweetgum) and *Zea mays* (maize) expressing tobacco anionic peroxidase have exhibited increased resistance to insects. (Dowd, et al., 1999). Different species of insects were fed transgenic leaves from the above plants. Some insects displayed increased mortality and decreased body weight compared to those insects fed control leaves. (Id.). Researchers suggested that resistance was achieved due to a combination of three peroxidase-generated factors: enhanced tissue toughness, decreased nutritional quality, and enhanced toxicity. The enhanced toxicity was considered to be the main factor.

It is believed that a specific nematode-upregulated peroxidase promoter could be very valuable, and the regulation of a phytotoxic gene by such a promoter could destroy nematode feeding sites and confer resistance. To date, no nematode-upregulated promoters have been cloned from monocots and individual peroxidase genes associated with nematode expression have not been characterized.

In this regard, one aspect of the present invention is the isolation and characterization of the gene sequence which encodes the peroxidase P7X gene isolated from maize inbred line Mp307 as well as the gene sequence which encodes the upregulated peroxidase promoter for the peroxidase P7X gene isolated from maize inbred line Mp307.

The full P7X peroxidase gene sequence was assembled from ten independent clones obtained by rapid amplification of 5'- and 3'-cDNA ends (RACE) and one clone obtained by genomic walking. In particular, the 3'-RACE (SEQ ID NO. 3) was performed with Jprim (3'-GTGCCCCAACGCGCTGTCCACCATCAA) and 5' RACE (SEQ ID NO. 4) with P75w1 (5'-GCCC TAGCAGAACTGTCCACGAAGGCCCGCCGAGC) gene-specific primers. A schematic illustration of the assembly of the P7X peroxidase gene using these clones is shown in FIG. 1.

RACE allows for the selective amplification of the 5'- or 3'-end of cDNA that has an adapter of the subject invention attached at both ends of the cDNA. By using a combination of an internal target DNA primer that is complementary to a portion of the nucleotide sequence of the target DNA and a primer that is complementary to the primer binding portion of the adapter, only the 5'- or 3'-end of any individual RNA is exponentially amplified during the polymerase chain reaction (PCR) step. The non-target cDNAs that lack the internal primer binding sequence that is specific to the target cDNAs are not efficiently amplified.

The 5'- and 3'-RACE amplification products obtained from PCR are then fused to create a full length cDNA. The 5'- and 3'-RACE products are purified and then mixed together in the absence of primers. The mixture is subjected to several rounds of PCR cycling in the presence of a DNA polymerase. The overlapping regions of the RACE products anneal and are then extended to generate the full length cDNA.

Genomic walking is a technique whereby overlapping DNA fragments are sequentially isolated in order to "walk" up or down a larger polynucleotide segment, such as a chromosome. In the first cycle of genomic walking, a subfragment from one end of the first clone is used to isolate clones that extend farther along the chromosome. (Lewin, 2000). In subsequent cycles, a new clone that has a restriction map that coincides at one end with the end of the previous clone and has new material at the other end is selected. (Id.). Cycles of clone selection are repeated until the full length sequence is obtained.

Sequence analysis of the independent RACE clones obtained in the present invention revealed that P7X peroxidase mRNA could be polyadenylated at various sites. (See FIG. 1). Further computer analysis revealed a putative signal peptide coding sequence. The P7X peroxidase was predicted to be almost neutral (pI=6.74) with extracellular localization. As shown in FIG. 3, the total P7X peroxidase gene sequence was estimated to be 1379 bp.

The P7X peroxidase promoter was isolated by genomic walking, (Padegimas, et al., 1998). An additional P72w2 (SEQ ID NO. 5) (5'-AGATTCGGGCCCTGGCTCTGCTCCCCTGACGTGTC) nested primer was utilized to increase the walking specificity and identify any regulatory sequences that may be present. It can be seen in FIG. 1 that the comparative sequence analysis of the clone (2B) obtained by genomic walking with the P7X peroxidase mRNA sequence revealed a 108 nt intron located at position 227 of the coding sequence. It was determined that this intron is bordered by unusual nonconsensus sequences, specifically 5'-GG<u>GC</u>---<u>AG</u>CC. The P7X peroxidase promoter was estimated to be 1000 bp in length, as shown in FIG. 4.

Figure 2:
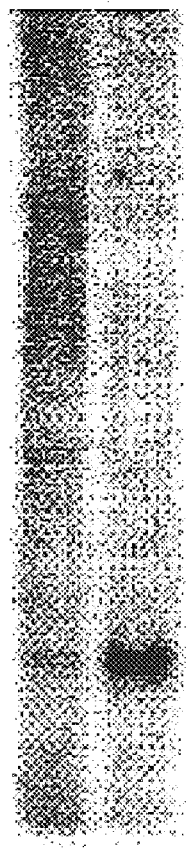
FIG. 2 is a photograph of a Northern Blot analysis for the expression of P7X peroxidase in roots.

In a further experiment, radioactively labeled probes were prepared using the 3'- noncoding region of the P7X peroxidase gene. Northern blot analysis of RNA isolated from nematode-inoculated and control maize Mp 307 roots that revealed the P7X peroxidase gene is up-regulated in nematode-inoculated roots. (See FIG. 2).

It is believed that the P7X peroxidase gene and the P7X peroxidase promoter can be used to fight nematode infection in plants. Four independent scenarios are suggested for obtaining nematode resistance in plants.

In the first scenario, it is hypothesized that the P7X gene driven by the P7X promoter can be used to induce a hypersensitive resistance response in root-knot nematode-infected plant roots. The possible candidates to promote a plant defense response include peroxidase genes which are known to be involved in hypersensitive responses, including signal transduction-induced resistance. Increased peroxidase activity has been observed in a number of resistant interactions involving plant-pathogenic fungal and bacterial interactions, such as the increased level of anionic peroxidase activity that has been discovered in resistant tomatoes after nematode inoculation. (Zacheo, et al., 1993). The P7X peroxidase gene of the present invention has been shown to be induced in the root-knot nematode-resistant maize inbred line Mp307. Therefore, it is believed that the P7X peroxidase gene, driven by it native P7X promoter or other nematode-inducible promoters, could be utilized to obtain nematode resistance in transgenic plants. Other possible gene candidates involved in plant responses to pathogen attacks are described in Stintz, et al. (1993).

In accordance with the second scenario, it is hypothesized that the P7X peroxidase gene can be fused to a chimeric promoter for constitutive expression, (e.g., using the 35S promoter from the cauliflower mosaic virus (CaMV) (Benfey and Chua, 1990) or for more regulated expression (e.g. tissue specific promoter, inducible promoter, etc.). The 3'- untranslated sequences could be from the P7X gene or from another plant-recognized gene. It has been determined that the introduction of a constitutively expressed peroxidase gene in transgenics was correlated with enhanced insect resistance in those plants (Dowd et al., 1999).

In accordance with the third scenario, it is believed that the expresssion of a gene toxic to nematodes in feeding site cells could poison the infecting nematodes, thereby debilitating them, or, if they are still motile, induce evacuation of the plant's roots. The use of the P7X peroxidase promoter would ensure that the toxin gene is expressed only, or substantially only, in cells surrounding the nematodes. This specificity would avoid any potential deleterious effects to the plant. In this regard, nucleic acid constructs are proposed which would allow for the expression of a toxin in a plant in response to nematode infection and provide an active defense response to root-knot nematodes.

The term "operatively linked" as used herein refers to DNA sequences on a single DNA molecule which are associated such that the function of one is affected by the other. A promoter is operatively linked with a structural gene when it is capable of affecting the expression of that structural gene. In other words, the structural gene is under the transcriptional control of the promoter. The promoter is said to be upstream from the structural gene and the structural gene is said to be downstream from the promoter.

The term "constructs" or "transcription cassettes" includes, in the 5' to 3' direction, a structural gene or a series of structural genes operatively linked to the promoter sequence or element, and optionally a termination sequence including a stop signal for RNA polymerase. All of these regions should be capable of operating in the cells of the tissue to be transformed. Any suitable termination sequence may be employed. The same is true for the term "fused" in relation to the present invention which includes direct or indirect attachment.

A proposed nucleic acid construct of the present invention is formed of the P7X peroxidase promoter of the present invention operatively linked to a toxin specific for nematodes. The toxin is inserted downstream from and under the regulation of the P7X peroxidase promoter. The peroxidase promoter provides for the initiation of the transcription of the toxin when nematode infection occurs.

A wide variety of toxins could be used, and would be easily identifiable by one of ordinary skill in the art. Examples of such toxins for use in the present invention include genes encoding *Bacillus thuringiensis* toxins described in EP 517,367 A1, genes encoding proteinase inhibitors such as cowpea trypsin inhibitor described in WO 92/15690, and genes encoding proteins such as miraculin that effect nematode sensory behavior.

The term "transgenic" in relation to the present invention does not include a promoter in its natural environment in combination with its associated gene or series of genes in its natural environment. Thus, the term includes seedlings or plants incorporating a gene or a series of genes which may be natural or non-natural to the seedling or plant operatively linked to the inducible gene promoter sequence or element of the present invention.

A transgenic plant is one which has been genetically modified to contain and express foreign DNA sequences. As specifically exemplified herein, a transgenic plant is genetically modified to contain and express a DNA sequence operably linked to and under the regulatory control of transcription control sequences which it is not normally regulated. Thus, when a DNA construct of the present invention is incorporated into plant cells, and these cells replicated to generate a plant, a transgenic plant is formed. As used herein, a transgenic plant also refers to those progeny of the initial transgenic plant which carry and are capable of expressing a toxin in response to nematode infection. Seeds containing transgenic embryos are encompassed within this definition.

Methods of making transgenic nematode-resistant plants involve providing a plant cell capable of regeneration. The plant cell is then transformed with a DNA construct, and a recombinant nematode-resistant plant is regenerated from the transformed plant cell on appropriate selective media depending on the plant and vector used for transformation. Any cell tissue capable of propagation may be transformed. Transformation can occur by a number of well-known methods suitable for forming a transgenic plant, such as by introducing a transcription cassette into a plasmid vector specialized for plant transformation via *Agrobacterium tumefaciens* or by biolistic microparticle bombardment. Other methods of transformation would be known by one of ordinary skill in the art. Methods of maize transformation and examples thereof are set forth in U.S. Pat. No. 6,140,555 and U.S. application Ser. No. 09/698,080, both of which are incorporated by reference in their entirety.

The P7X peroxidase promoter may be active in both monocots and dicots (eudicots), and techniques are well-known in the art for the induction of DNA into monocots as well as dicots (eudicots), as are the techniques for culturing such plant tissues and regenerating those tissues. As a result, a wide variety of plant species can be used in accordance with the present invention.

In the fourth proposed scenario, it is hypothesized that the P7X peroxidase promoter can be fused to a gene encoding a toxin which is toxic to plants for the induced prevention of giant cell formation in root-knot nematode-infected plants. It is believed that the induction of a plant toxin gene could kill the plant cells that are involved in providing nutrients to the nematode or suppress the development of the giant cells which are critical for nematode survival and reproduction, thereby either killing the nematode or forcing it to leave the root.

The plant toxin gene can be chosen from variety of genes that are capable of killing plant cells, disabling parenchyma cell development into feeding cells, or promoting a plant defense response, such as a hypersensitive response, that leads to cell death and signal transduction-induced resistance. The toxic product may either kill the plant cell in which it is expressed or simply disable the cell so that it is less capable of supporting the pathogen. It is preferred, especially where the plant is a food plant, that the plant-toxic product be non-toxic to animals, and particularly be non-toxic to humans.

Specific examples of genes that are capable of killing or disabling a plant cell include genes encoding proteases (e.g. trypsin, pronase A, carboxypeptidase, variety of endoproteinases), genes encoding ribosome inactivating proteins (RIPs) (e.g. RIP encoding genes from *Phytolacca americana, Phytolacca insularis, Phytolacca dioica, Phytolacca dodecandra*), genes encoding nucleases (e.g barnase, RNase A, RNase T, RNase CL-3, variety of DNA exonucleases and endonucleases including restriction nucleases), genes encoding lipases (e.g. lipases from porcine pancrease and *Candida cyclindracea*), genes encoding membrane channel proteins (e.g. glp F and connexins), genes encoding antibodies targeted to plant cell essential proteins (e.g. RNA polymerase, respiratory enzymes, protein kinases, Krebs cycle enzymes, cytochrome oxidase, aminocyclopropane-1-carboxylic acid synthase, and enzymes involved in the shikimic acid pathway such as enolpyruvyl shikimic acid-5-phosphate synthase), genes encoding antisense RNA or ribozymes targeted to plant cell essential proteins mentioned above, and genes encoding toxins from plant pathogens (e.g., phaseolotoxin, tabtoxin, and syringotoxin).

Examples of genes that can disable the development of plant cells into the giant cell feeding sites for root-knot nematodes include genes that encode antibodies targeted to nematode injected proteins that induce feeding site formation and genes that encode antibodies targeted to plant proteins, hormones, or signal elements (of signal transduction pathway) that are produced in response to nematode attack and which play a critical role in the giant cell feeding site formation.

Having generally described this invention, a further understanding can be obtained by reference to certain specific examples which are provided herein for purposes of illustration only and are not intended to be limiting unless otherwise specified.

EXAMPLE

Isolation of P7X Gene and Promoter

Plant Material

*Zea mays* (maize inbred line Mp307) seedlings were inoculated with 5000 root-knot nematode (race 4) eggs. Both infected and control plants were grown for 9 additional days under greenhouse conditions. RNA extracted from these plants was used for RNA Northern gel blot analysis, cDNA synthesis, reverse transcription (RT) PCR, and for generation of adaptor-ligated libraries (for RACE).

Plant Genomic DNA Isolation

Plant genomic DNA was isolated from *Zea mays* (maize inbred line Mp307) leaves. Polysaccharides were removed by ethanol precipitation.

RNA Isolation

Total RNAs were isolated from inoculated and control roots using TRIzol® reagent (Gibco BRL) and an additional polysaccharide precipitation with 30% ethanol. The mRNA was purified with Dynabeads® (DYNAL).

Northern Gel Blot Analysis

Ten $\mu$g of total RNA was separated by agarose gel electrophoresis containing glyoxal/dimethyl sulfoxide. The RNA was transferred to GeneScreen Plus (DuPont) membranes using a downward alkaline capillary transfer procedure and was fixed by a microwave oven. Hybridizations were performed in ExpressHyb (Clontech) solution supplemented with a [$\alpha$-$^{32}$P]dATP-labeled probe. The probe was obtained using Stratagene Prime-It II random primer labeling kit.

Subcloning

PCR fragments were ligated into pBluescript II KS (−) vector followed by transformation in XL-1 *E. coli* competent cells, with growth and selection on LB medium containing ampicillin. Recombinant clones were selected by PCR. All of these techniques are amply exemplified in the literature and are well-known to those of ordinary skill in the art. Particular exemplification is found in Sambrook et al., 1989.

Sequencing and Analysis

Sequencing was performed using manual as well as automatic sequencing methods. Manual sequencing was performed with a Thermo Sequenase radiolabeled terminator cycle sequencing kit (Amersham). Automatic sequencing was performed using a flourescent terminators kit (Perkin Elmer) and an ABI310 sequencing system. Sequence analysis was performed with Lasergene (DNASTAR Inc.), PSORT (Nakai, K., Genomenet, Kyoto, Japan) and SignalP programs.

RT PCR Analysis cDNA was synthesized using mRNA isolated from inoculated and control roots. PERPROM primer was employed for first strand cDNA synthesis. The cDNA was amplified using PERPROM and one peroxidase-specific (Hprim, Jprim or Kprim) primer. The mRNAs from inoculated and control roots were used as templates for negative controls.

RACE cDNA corresponding to inoculated and control roots were synthesized and amplified. 5'-GAAGAATTCTCGAGCGGCCGC(T)$_{19}$V; IDT® Inc. (SEQ ID NO. 6) was used for initiation of first strand cDNA and an additional primer (5'-pGAAG AATTCTCGAGCG-GCCGC; IDT® Inc.) (SEQ ID NO. 7) was added for cDNA amplification. Jprim (SEQ ID NO. 3) (5'-GTGCCCCAACGCGCTGTCCACCATCAA) was used for 3'-RACE and P75w1 (SEQ ID NO. 4) (5'-GCCC TAGCAGAACTGTCCACGAAGGCCCGCCGAGC) was used for 5'-RACE.

Each adaptor-ligated cDNA library was prepared by the following method.

The PCR reaction mix was extracted twice with phenol:chloroform (1:1; v/v). DNA was precipitated by the addition of 0.5 vol. of 6.0 M ammonium acetate, 20 μg glycogen (Boehringer Mannheim) and 2.5 vol. ethanol. The samples were then incubated for 20 min. at −80° C. and centrifuged at 1600 ×g in a microcentrifuge for 15 min. Each pellet was washed twice with 85% ethanol, air dried, and dissolved in 20 μl H$_2$O. Approximately 2.0 μg cDNA (amount was estimated fluorometrically) was polished with 12 U T4 DNA polymerase (New England BioLabs) in 40 μl T4 DNA polymerase buffer (1×) saturated with 250 μm dNTP for 30 min at 16° C. Polished cDNA was extracted with phenol:chloroform, precipitated, washed, and dissolved in water as described above. The cDNA was then ligated with 50 pmol of a walking adaptor for 8 hours at 16° C. using 10 U T4 DNA ligase (Fermentas) in 20 μl reaction volume using ligation buffer containing 40 mM Tris-HCl pH 7.8, 10 mM MgCl$_2$, 10 mM DTT, and 0.5 mM ATP. The reaction was terminated by a 15 min. incubation at 75° C., then diluted to 39 μl. One μl Exo III (200 U, Fermentas) was added. The reaction mix was incubated for 12 hours at 37° C. and then terminated by a 15 min. incubation at 75° C. Adaptor-ligated cDNA libraries were stored at 20° C.

RACE was performed in 50 μl total volume which contained 1 × Tth PCR reaction buffer [40 mM Tris-HCl (pH 9.3 at 25° C.), 15 mM KOAc; Clontech], 200 μM dNTP (Boehringer Mannheim), 1.0 mM Mg(OAc)$_2$, 0.2 μM each adaptor-specific (APN) and gene-specific primers, 1.0 μl adaptor-ligated cDNA library and 1.0 μl 50× Advantage™ Tth polymerase mix. PCRs were conducted using thin-walled tubes in a thermocycler. The thermocycler was programmed for 36 cycles: 10 sec. at 95° C. and 3 min. at 67–73° C. (dependent on primer optimal annealing temp.) with a 4 min. extension for the last cycle.

Genomic Walking

Walking in genomic DNA was performed on genomic DNA isolated from maize inbred line Mp307 leaves. Polysaccharides were removed by ethanol precipitation. DNA concentration was estimated fluorometrically using Hoechst 33258 dye.

The walking adaptor consisted of two oligonucleotides (LN and Oligo1) that are partially complementary to each other and form unique secondary structure; LN 5' CAGCA-GAACGACGCCCCGCCGACAAGGACAGGT (SEQ ID NO. 8) (longer adaptor strand), Oligol: 5' ACCTGTCCT-GCGAAAGCAsAsAsA (SEQ ID NO. 9) (shorter adaptor strand). Adaptor-specific primer APN was utilized in each RACE or walking experiment; APN 5' CAGCAGAAC-GACGCCCCGCCGACAA (SEQ ID NO. 10). The primer used in genomic walking was P75w2 (SEQ ID NO. 5) (5'-AGATTCGGGCCCTGGCTCTGCTCCCCTGA CGTGTC).

Five libraries were prepared using five different restriction endonucleases: BamHI, DraI, EcoRV, ScaI, and SspI. For each library, 10 μg maize genomic DNA was digested in 200 μl reaction volume with 100 U of appropriate restriction enzyme for 4 h at 37° C. buffer which also contained 0.1 mg/ml BSA and 0.3 mg/ml boiled RNase A. Following digestion with BamHI, 8.0 μl 2.5 mM dNTP and 2.0 μl (10 U) Klenow fragment of E.coli DNA polymerase I were added and then further incubated for 15 min. at room temperature. Five microliters of each reaction mix was loaded onto a 1.0% agarose gel to determine digestion efficiency. The remaining DNA was extracted twice with phenol/chloroform (1:1; v/v) and then precipitated by addition of 0.5 vol. 6.0 M ammonium acetate, 20 μg glycogen (Boehringer-Manheim), and 2.5 vol. ethanol. After mixing, the tubes were incubated for 20 min. at −80° C. and centrifuged at 16,000g in a microcentrifuge for 15 min. Each pellet was washed twice with 85% ethanol, air dried, and dissolved in 20 μl H$_2$O.

The shorter strand adaptor oligonucleotide (1600 pmol) was phosphorylated using 40 U polynucleotide kinase in 40 μl buffer saturated with 1 mM ATP for 1 h at 37° C. and then terminated by 10 min. incubation at 75° C. The longer strand adaptor (LN; 1600 pmol) was added, and then the mixture was heated for 1 min. at 75° C. and incubated for 1 h at room temperature for annealing. Adaptors were extracted twice with phenol/chloroform and then precipitated by addition of 0.1 vol. 3.0 M sodium acetate, pH 5.2, 20 μg glycogen, and 3 vol. ethanol following by 20 min. incubation at −80° C. and 20 min. centrifugation in a microcentrifuge at 16,000g. The DNA pellet was washed twice with 85% ethanol, air dried, and dissolved in 20 μl H$_2$O.

One-half of the digested genomic DNA (approximately 5.0 μg) was ligated with 50 pmol adaptor for 20 h at 16° C. using 10 U T4 DNA ligase in 20 μl reaction volume with a buffer. The reaction was terminated by 15 min. incubation at 75° C. It was then diluted with 180 μl H$_2$O. Exo III (1.0 μl; 200 U) was added and incubated for 20 h at 37° C. The reaction was terminated by 15 min. incubation at 75° C. Adaptor ligated genomic libraries were stored at −20° C.

Each PCR (50 μl total volume) contained 1× Tth PCR buffer [40 mM Tris-HCl (pH 9.3 at 25° C.), 15 mM potassium acetate; Clontech], 200 μM dNTPs (Boehringer-Mannheim), 1.1 mM magnesium acetate, 0.2 μM each APN and 3Zeal primers, 1.0 μl (approximately 25 ng) library DNA, and 1.0 μl 50× Advantage Tth polymerase mix. All reactions were carried out in thin-walled tubes. PCRs were conducted in a thermal cycler programmed for 7 cycles at 2 sec. at 93° C. and 3 min. at 72° C., followed by 32 cycles at 2 sec. at 93° C., 3 min. at 67° C., and 4 min. extension for the last cycle.

The invention of this application is described above both generically, and with regard to specific embodiments. A wide variety of alternatives known to those of ordinary skill in the art can be selected within the generic disclosure, and examples are not to be interpreted as limiting, unless specifically so indicated. The invention is not otherwise limited, except for the recitation of the claims set forth below. All references cited herein are incorporated in their entirety.

What is claimed is:

1. An isolated DNA sequence having the sequence of SEQ ID NO:2, said DNA sequence being a nematode-inducible promoter and capable of inducing nematode resistance in plants.

2. A vector comprising the isolated DNA sequence of claim 1.

3. A host cell comprising the vector of claim 2.

4. A DNA construct comprising, in the 5' to 3' direction of transcription, a promoter, a gene encoding a toxin positioned downstream from said promoter and operatively linked thereto, wherein said promoter is a nematode-inducible promoter having the sequence of SEQ ID NO:2.

5. The DNA construct of claim 4, wherein said promoter is up-regulated by nematodes.

6. The DNA construct of claim 4, wherein said toxin is toxic to nematodes.

7. The DNA construct of claim 4, wherein said toxin is toxic to plant cells and is capable of killing or disabling a plant cell so that it cannot nutritionally support a nematode.

8. The DNA construct of claim 4, wherein said gene encoding a toxin is selected from the group consisting of genes encoding trypsin, genes encoding pronase A, genes encoding carboxypeptidase, genes encoding ribosome inactivating proteins from *Phytolacca americana*, genes encoding ribosome inactivating proteins from *Phytolacca insularis*, genes encoding ribosome inactivating proteins from *Phytolacca dioica*, genes encoding ribosome inactivating proteins from *Phytolacca dodecandra*, genes encoding barnase, genes encoding RNase T, genes encoding RNase CL-3, genes encoding phaseolotoxin, genes encoding tabtoxin, genes encoding syringotoxin, and genes encoding *Bacillus thuringiensis* toxins.

9. The DNA construct of claim 4, wherein said promoter is isolated from maize inbred line Mp307.

10. A transcription cassette comprising, in the 5' to 3' direction of transcription, a promoter, a gene encoding a toxin positioned downstream from said promoter and operatively linked thereto, wherein said promoter is a nematode-inducible promoter having the sequence of SEQ ID NO:2.

11. The transcription cassette of claim 10, wherein said promoter is up-regulated by nematodes.

12. The transcription cassette of claim 10, wherein said toxin is toxic to nematodes.

13. The transcription cassette of claim 10, wherein said toxin is toxic to plant cells and is capable of killing or disabling a plant cell so that it cannot nutritionally support a nematode.

14. The transcription cassette of claim 10, wherein said gene encoding a toxin is selected from the group consisting of genes encoding trypsin, genes encoding pronase A, genes encoding carboxypeptidase, genes encoding ribosome inactivating proteins from *Phytolacca americana*, genes encoding ribosome inactivating proteins from *Phytolacca insularis*, genes encoding ribosome inactivating proteins from *Phytolacca dioica*, genes encoding ribosome inactivating proteins from *Phytolacca dodecandra*, genes encoding barnase, genes encoding RNase T, genes encoding RNase CL-3, genes encoding phaseolotoxin, genes encoding tabtoxin, genes encoding syringotoxin, and genes encoding *Bacillus thuringiensis* toxins.

15. A transgenic nematode-resistant plant comprising transformed plant cells containing the DNA construct of claim 4.

16. A method of providing nematode resistance in plants comprising preparing a DNA construct comprising a transcription cassette, said DNA construct comprising, in the 5' to 3' direction of transcription, a promoter, a gene encoding a toxin positioned downstream from said promoter and operatively linked thereto, wherein said promoter is a nematode-inducible promoter having the sequence of SEQ ID NO:2; transforming nematode susceptible plant cells with said DNA construct, wherein said transformed plant cells exhibit resistance to nematodes;

regenerating said transformed plant cells to produce a transgenic plant having nematode resistance.

17. The method of claim 16, wherein said promoter is up-regulated by nematodes.

18. The method of claim 16, wherein said toxin is toxic to nematodes.

19. The method of claim 16, wherein said toxin is toxic to plant cells and is capable of killing or disabling a plant cell so that it cannot nutritionally support a nematode.

20. The DNA construct of claim 4 further comprising a termination sequence positioned downstream from said gene encoding a toxin and operatively linked thereto.

21. The transcription cassette of claim 10 further comprising a termination sequence positioned downstream from said gene encoding a toxin and operatively linked thereto.

22. The method of claim 16, wherein said DNA construct further comprises a termination sequence positioned downstream from said gene encoding a toxin and operatively linked thereto.

\* \* \* \* \*